US010337935B2

(12) United States Patent
Geiger et al.

(10) Patent No.: US 10,337,935 B2
(45) Date of Patent: Jul. 2, 2019

(54) SYSTEMS AND METHODS FOR INTEGRATED, MULTI-FUNCTIONAL, FAULT TOLERANT SENSING AND COMMUNICATION

(71) Applicant: Sikorsky Aircraft Corporation, Stratford, CT (US)

(72) Inventors: Derek Geiger, Wilton, CT (US); Marcus D. Cappelli, Shelton, CT (US); Jonathan K. Garhart, Seymour, CT (US); Avinash Sarlashkar, Pittsford, NY (US); Andrew Brookhart, Wallingford, CT (US); Mark W. Davis, Southbury, CT (US)

(73) Assignee: SIKORSKY AIRCRAFT CORPORATION, Stratford, CT (US)

( * ) Notice: Subject to any disclaimer, the term of this patent is extended or adjusted under 35 U.S.C. 154(b) by 4 days.

(21) Appl. No.: 15/835,814

(22) Filed: Dec. 8, 2017

(65) Prior Publication Data
US 2018/0164526 A1    Jun. 14, 2018

Related U.S. Application Data

(60) Provisional application No. 62/432,942, filed on Dec. 12, 2016.

(51) Int. Cl.
*G01L 1/24* (2006.01)
*G01M 5/00* (2006.01)
(Continued)

(52) U.S. Cl.
CPC ............. *G01L 1/242* (2013.01); *G01L 1/24* (2013.01); *G01M 5/0016* (2013.01);
(Continued)

(58) Field of Classification Search
CPC ..... G02B 6/4471; G02B 6/02033; G01L 1/24; G01L 1/242; G01M 5/0016;
(Continued)

(56) References Cited

U.S. PATENT DOCUMENTS 8,417,113 B1    4/2013  Harres
9,064,357 B1    6/2015  McCormick
(Continued)

FOREIGN PATENT DOCUMENTS

| EP | 2693187 A2 | 2/2014 |
|---|---|---|
| WO | 0037925 | 6/2000 |
| WO | 2015183364 A2 | 12/2015 |

OTHER PUBLICATIONS

EP Extended Search Report dated May 14, 2018 cited in Application No. 17206716.7, 8 pgs.

*Primary Examiner* — Michael P Mooney
(74) *Attorney, Agent, or Firm* — Cantor Colburn LLP

(57) ABSTRACT

A fiber-optic sensor system includes a structure having a fiber-optic cable operatively connected thereto. The system includes a network controller with an interrogator operatively connected to the fiber-optic cable to receive optical energy indicative of a characteristic of the structure therefrom and convert optical energy to electrical energy and electrical energy to optical energy for data communication. A sensor and/or a data source are operatively connected to the fiber-optic cable through the network controller to transmit data through the fiber-optic cable and receive data therefrom.

15 Claims, 3 Drawing Sheets

(51) Int. Cl.
　　　*H04B 10/071*　　　(2013.01)
　　　*G01M 11/08*　　　(2006.01)
　　　*G02B 6/02*　　　(2006.01)
　　　*G02B 6/44*　　　(2006.01)
　　　*B64D 45/00*　　　(2006.01)
　　　*G01N 21/84*　　　(2006.01)
　　　*G07C 5/08*　　　(2006.01)

(52) U.S. Cl.
　　　CPC ........ G01M 5/0033 (2013.01); G01M 5/0041 (2013.01); G01M 5/0091 (2013.01); G01M 11/083 (2013.01); G02B 6/02033 (2013.01); G02B 6/4471 (2013.01); H04B 10/071 (2013.01); *B64D 2045/0085* (2013.01); *G01N 2021/8472* (2013.01); *G07C 5/0816* (2013.01)

(58) Field of Classification Search
　　　CPC ............. G01M 5/0033; G01M 5/0041; G01M 5/0091; G01M 11/083; H04B 10/071; B64D 2045/0085; G01N 2021/8472; G07C 5/0816
　　　USPC ............................................. 385/12, 13, 100
　　　See application file for complete search history.

(56) References Cited

U.S. PATENT DOCUMENTS

| | | |
|---|---|---|
| 9,170,172 B2 | 10/2015 | Hunt et al. |
| 9,274,025 B2 | 3/2016 | Okoli et al. |
| 2015/0211969 A1* | 7/2015 | Muller ................. G01P 15/093 73/849 |
| 2015/0370030 A1 | 12/2015 | Sutton et al. |

* cited by examiner

SYSTEMS AND METHODS FOR INTEGRATED, MULTI-FUNCTIONAL, FAULT TOLERANT SENSING AND COMMUNICATION

CROSS-REFERENCE TO RELATED APPLICATIONS

The present application claims the benefit under 35 U.S.C. § 119(e) of U.S. Provisional Patent Application Ser. No. 62/432,942 filed on Dec. 12, 2016, which is incorporated herein by reference in its entirety.

BACKGROUND OF THE INVENTION

1. Field of the Invention

The present disclosure relates to sensing and communication systems and methods, and more particularly to systems and methods for fiber-optic sensing and communication networks.

2. Description of Related Art

Structures such as aircraft airframes, and particularly rotorcraft structures, are susceptible to conditions that impose certain characteristics or alter pre-existing characteristics of the structures. Traditional methods to sense and/or monitor these characteristics involve wire harnesses and sensors. Communications across air vehicle components, separate from communicating sensor data, can also be transferred through wire harnesses. Wire harnesses can be heavy and difficult to install, whether for sensing or for communication.

Such conventional methods and systems have generally been considered satisfactory for their intended purpose. However, there is still a need in the art for improved methods and systems for leveraging advanced communications, advanced sensing, and advanced fault tolerance. The present disclosure provides a solution for this need.

SUMMARY OF THE INVENTION

A fiber-optic sensor system includes a structure having a fiber-optic cable operatively connected thereto. The system includes a network controller with an interrogator operatively connected to the fiber-optic cable to receive optical energy indicative of a characteristic of the structure therefrom and convert optical energy to electrical energy and electrical energy to optical energy for data communication. A sensor and/or a data source are operatively connected to the fiber-optic cable through the network controller to transmit data through the fiber-optic cable and receive data therefrom.

In accordance with some embodiments, the data source is an avionics or flight control system to provide data through the fiber optic cable to the network controller and to receive data through the fiber optic cable from the network controller. The avionics system can include a health monitoring system and/or a rotor state feedback system operatively connected to the fiber-optic cable through the network controller to transmit data to the network controller and through the fiber-optic cable and to receive data therefrom.

The fiber-optic cable can be embedded within the structure. The structure can be one of a plurality of structures wherein the fiber-optic cable extends between adjacent structures. The structure can include an access point to provide physical access to the fiber-optic cable within the structure, and/or a port to provide connection access to the fiber-optic cable and the network controller. A sensing element can be inserted within the fiber-optic cable to modify optical energy in a way that is indicative of a characteristic of the structure and to transmit or reflect back energy received from/to the network controller. The network controller can include at least one optical component selected from a group consisting of an amplifier, a connector, a switch, a receiver, a laser diode, a photodiode, and a transmitter.

In accordance with another embodiment, a method for integrally sensing and communicating through a structure includes transmitting optical energy indicative of a characteristic of a structure through a fiber-optic cable to an interrogator in a network controller. The method includes transmitting data from at least one of a sensor or a data source from the network controller through the fiber-optic cable.

In accordance with some embodiments, the method includes detecting damage in the fiber-optic cable with a health monitoring system operatively connected to the network controller. The fiber-optic cable can be part of a fiber-optic network. The method can include mitigating faults within the fiber-optic network with the network controller by adjusting the configuration of the fiber-optic network to achieve fault tolerance. Adjusting the configuration of the fiber-optic network can include using at least one of an optical switch or the network controller to reconfigure the transmitting of optical energy from the fiber-optic cable to a second fiber-optic cable within the fiber-optic cable network. The method can include converting electrical energy to optical energy and vice versa. Transmitting data from the data source can include transmitting avionics data through the fiber-optic cable to the network controller from an avionics system. Transmitting data from the data source can include transmitting data through the fiber-optic cable from the network controller to the avionics system.

In accordance with another embodiment, an aircraft includes a structure and a fiber-optic cable operatively connected to the structure. A network controller having an interrogator is operatively connected to the fiber-optic cable to receive optical energy indicative of a characteristic of the structure therefrom. At least one of a data source or a sensor is operatively connected to the fiber-optic cable through the network controller to transmit data through the fiber-optic cable and receive data therefrom.

In accordance with some embodiments, the data source is an avionics system that provides avionics data through the fiber optic cable to the network controller and to receive data through the fiber optic cable from the network controller. The avionics system can include a health monitoring system and/or a rotor state feedback system. The fiber-optic cable can be embedded within or attached to the structure.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION OF THE PREFERRED EMBODIMENTS

Figure 1:
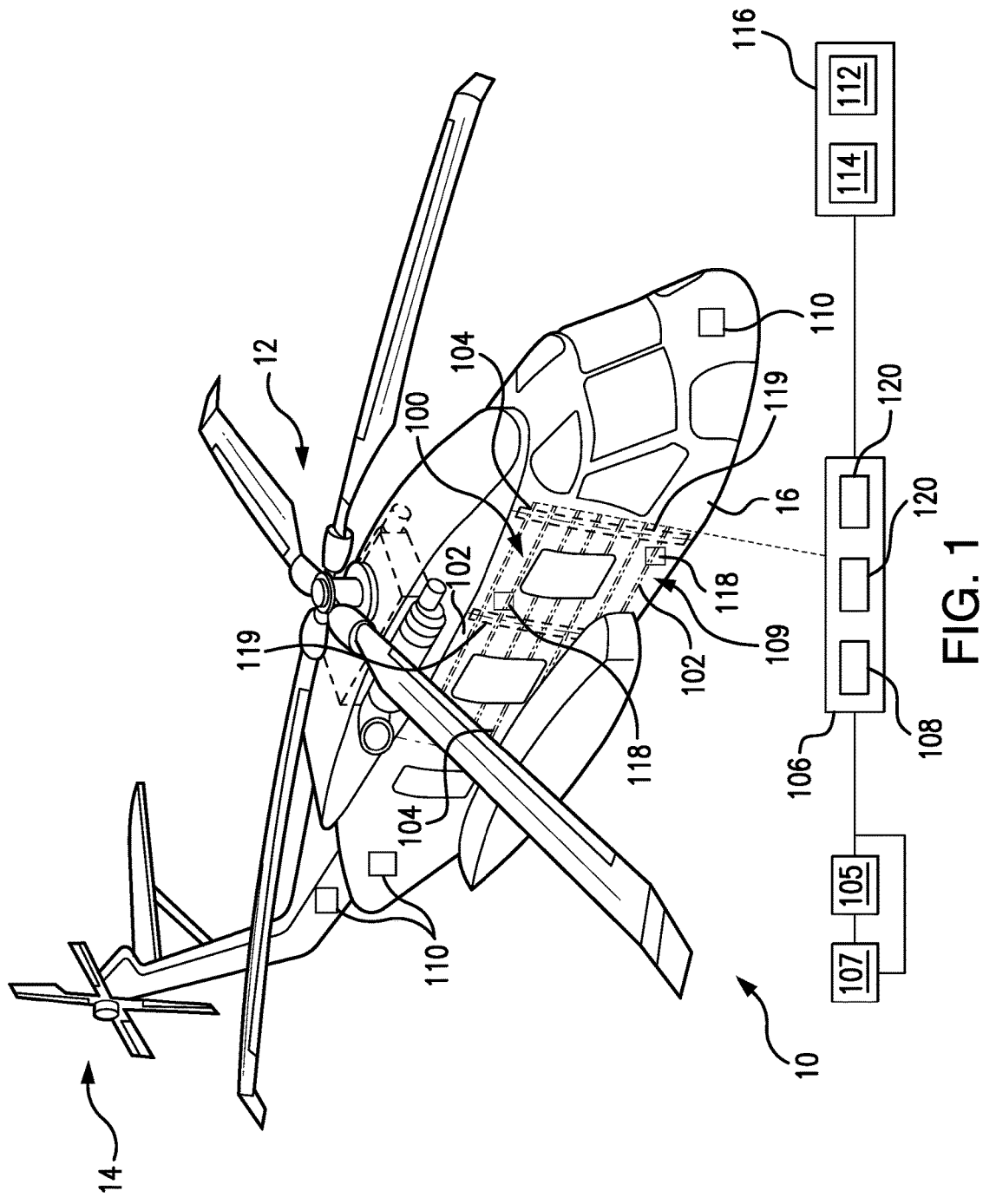
FIG. 1 is a schematic view of an embodiment of a vertical take-off and landing (VTOL) aircraft, showing a schematic view of an embodiment of a fiber-optic sensing and communication system constructed in accordance with the present disclosure.

Reference will now be made to the drawings wherein like reference numerals identify similar structural features or aspects of the subject disclosure. For purposes of explanation and illustration, and not limitation, a partial view of an exemplary embodiment of a vertical takeoff and landing (VTOL) aircraft in accordance with the disclosure is shown in FIG. 1 and is designated generally by reference character 10. Other embodiments of fiber-optic sensing and communication systems in accordance with the disclosure, or aspects thereof, are provided in FIGS. 2-3, as will be described. The systems and methods described herein provide low-weight, low-cost, high-bandwidth, and fault tolerant systems and methods for integral sensing and communication networks, thereby reducing susceptibility and vulnerability to damage and reducing the amount of maintenance required to detect, isolate, and repair faults within a sensor and communication network.

As shown in FIG. 1, VTOL aircraft 10 includes a main rotor system 12 and tail rotor system 14 supported by an airframe 16. Aircraft 10 includes a fiber-optic sensor system 100 with structures 102. Structures 102 can be a variety of aircraft components such as aircraft frames, beams, rotor blades, skin structure, gearbox housings, landing gear and other primary and secondary structural components. Structures 102 can be made from a variety of materials such as metallic or composite materials. Structures 102 have a plurality of fiber-optic cables 104. Fiber optic-cables 104 can also be operatively connected to structures 102, but not necessarily embedded therein, similar to fiber optic cable 204a, described below. It is contemplated that fiber-optic cables 104 can be exclusively embedded within structures 102, exclusively outside of structures 102, but operatively connected thereto, or a combination of both. Fiber-optic cables 104 form a fiber-optic sensing and communication network 109 and extend between adjacent structures 102.

With continued reference to FIG. 1, system 100 includes a network controller 106 with an interrogator 108 operatively connected to each fiber-optic cable 104 to receive optical energy indicative of characteristics of structures 102 therefrom. An optical signal is applied to fiber-optic cables 104. Fiber-optic cables 104 then modify the existing signal in a way that is indicative of characteristics of structures 102, e.g. by using a Fiber Bragg Grating to directly or indirectly measure strain, temperature, pressure, humidity, vibration or other characteristics, or by other inherent sensing element within fiber-optic cables 104. Interrogator 108 converts optical energy indicative of a given structural characteristic into electrical signals indicative of the given characteristic of the structure or environment. This allows network controller 106 to monitor structural characteristics of structures 102 through a variety sensing elements within fiber-optic cables 104. The sensing elements are not shown in FIG. 1, but are similar to sensing elements 211, described below. The sensing elements can include a Fiber Bragg Grating, or other inherent features that allow physical phenomena such as strain, temperature, pressure, humidity, and vibration to be measured using the fiber and appropriate optical components. Reconfiguration is feasible because of one or more of the following aspects of embodiments of the subject invention: a) multiple sensor elements in close proximity either within the same fiber-optic cable 104 or within two or more fiber-optic cables 104 that are sensitive to the same characteristic of the structure or environment, b) network hardware and controller logic that enables interrogation of alternate sensor elements on one or more alternative fiber-optic cables or from either end of a given fiber-optic cable, and c) ability to efficiently add new cables, systems, and sensors to the network 109.

With continued reference to FIG. 1, fiber-optic cables 104 used for sensing, e.g. strain sensing, are also included in a highly redundant, high bandwidth, and reconfigurable communication network that is used to transmit data from traditional systems or subsystems, or other systems similar to avionics system 116 such as a flight control system. Network controller 106 is operatively connected to a processor 107 and/or data storage 105 for storing data therein, receiving data therefrom, or the like. A data source, e.g. an avionics system or flight control system 116, is operatively connected to network controller 106 through fiber-optic cables 104 to provide avionics data through fiber optic cables 104 to network controller 106. Avionics system 116 also receives data through fiber optic cables 104 from network controller 106, such as strain data from the sensing elements. Avionics system 116 can include a variety of specialty avionics systems such as a health monitoring system 112, e.g. to monitor structural and/or network heath, or a rotor state feedback system 114.

Multiple fiber-optic cables 104 in conjunction with multiple network controllers 106 allow for reconfiguration without physical repair in case of damage to one or more fiber-optic cables 104 or network components, e.g. sensing elements. Fiber-optic system 100 is able to be reconfigured because of multiple fiber-optic cables 104 and the multi-functional nature of fiber-optic cables 104, e.g. being able to communicate data and perform health monitoring of the host structure 102, e.g. strain sensing or structural damage or of the fiber optic sensor system and network 100. Communication and/or data transfer between network controller 106 and each cable 104 provides diagnostic information relative to whether communication is passed through each individual fiber or network component. Network controllers 106 adjust the network configuration based on path information and condition information of fiber-optic cables 104 and hardware elements of the system 100 and network 109. For example, if health monitoring system 112 detects damage (structural or network damage) in an area where a given fiber-optic cable 104 is having intermittent communication, network controller 106 removes that fiber-optic cable 104 from network 109 and shifts data communication and structural health monitoring to other fiber-optic cables 104 in network 109 that are located in a similar location and sensitive to the same characteristics of the structure or environment. Alternatively, network controller 106 may be able to mitigate a network fault by interrogating a sensor from a different end of fiber-optic cable 104. Additionally, the structural health monitoring capability provided by sensing elements within fiber-optic cables 104 enables both structural condition and location to be provided for structure 102 where fiber-optic cables 104 are connected to or embedded within. The multiple sensing elements also allow localization of fiber damage or network elements and network configuration to provide continued sensing and network communication Structures 102 include access points 119 to provide physical access to fiber-optic cable 104 within structure 102. Access points 119 provide direct physical access for maintenance of fiber-optic network 109, e.g. manual reconfiguration of the network, fiber repair, optical component replacement, and the like. Access points 119 are provided at joints between two adjacent structures 102. Structures 102 include ports 118 that provide connection access to the fiber-optic cables 104 and the network controller 106 included within. For example, ports 118 allow connection to a new sensor, device, or the like into fiber-optic cable network 109. Ports 118 allow for rapid expansion or rearrangement of fiber optic sensor system 100 through additional connections to support additional sensing elements within fiber-optic cables 104, sensors 110 external to fiber-optic cables 104, or to cover additional structures 102.

With continued reference to FIG. 1, network controller 106 includes at least one optical component 120, for example, an amplifier, a connector, a switch, a receiver, and/or a transmitter. Optical components, such as laser diodes, convert electrical energy to optical energy for data transmission and other optical components, such as photodiodes convert optical energy to electrical energy or signals for communication outside of system 100. Optical components 120 transfer optical data across rotating and non-rotating mechanical interfaces, and switch optical data flow between different fibers and interrogate fiber sensing elements from different directions along the fiber (e.g., reconfigures optical network to accommodate network faults). A plurality of sensors 110 are operatively connected to fiber-optic cables 104 through network controllers 106 to transmit data through the communication network of fiber-optic cables 104. Sensors 110 can also be connected to network controller 106 through a separate fiber-optic cable network or through fiber-optic cables 104. Sensors 110 can also be connected to network controller 106 through a traditional copper wire interface. Sensors 110 receive data from network controller 106 and/or fiber-optic cable 104. Sensors 110 are mounted to a variety of aircraft 10 components either within structures 102 or separate from structures 102, e.g. fuselage components. Portions of system 100, for example, sensors 110 and structures 102, can be on aircraft 10, while other portions, for example, processor 107 and/or data storage 105, can be on the ground. For example, ground support equipment can be used to interrogate health or trouble shoot system 100, network 109 or structure 102 as part of maintenance activities.

Those skilled in the art will readily appreciate that avionics systems, for example, rotor state feedback system 114 can include a separate fiber-optic sensor and communication system, similar to system 100, embedded within one or more rotor structures. A separate fiber-optic sensor and communication system for rotor state feedback system 114 may be necessary due to the higher frequency and/or sampling rate needed in some rotor systems and the need for data transmission between a fixed frame and a rotating frame.

As shown in FIG. 1, main rotor system 12 and tail rotor system 14, e.g. rotors, include a rotor state feedback system 114. Rotor state feedback system 114 is a specific type of avionics system that is operatively connected to both main and/or tail rotor systems 12 and 14, respectively. Rotor state feedback system 114 is operatively connected to fiber-optic cable 104 through network controller 106 to transmit rotor data from main and tail rotor systems 12 and 14 to network controller 106 and through fiber-optic cable 104. Rotor state feedback system 114 also receives data from network controller 106.

Multifunctional fiber-optic cables 104 provide structural sensing, e.g. in structures 102, and high bandwidth data communication network architecture. This tends to reduce weight and cost, as compared with traditional sensing and communication systems that rely on separate wire harnesses and/or networks. Data and/or characteristic data transmitted through fiber-optic cables 104 can be reconfigured by network controller 106, if needed, without physical access, thereby reducing mission aborts, maintenance, and downtime in case of damage to the optical-fiber network. Those skilled in the art will readily appreciate that while system 100 is described in the context of a VTOL aircraft, system 100 can be applied to all types of aircraft, vehicles, and other systems for which there is a desire to both communicate data within the system and to sense data within the system using a multi-functional fiber-optic sensing and communication system. For example, system 100 can be a communication system, an electrical system, a mechanical system, a structural system or any combination thereof.

Figure 2:
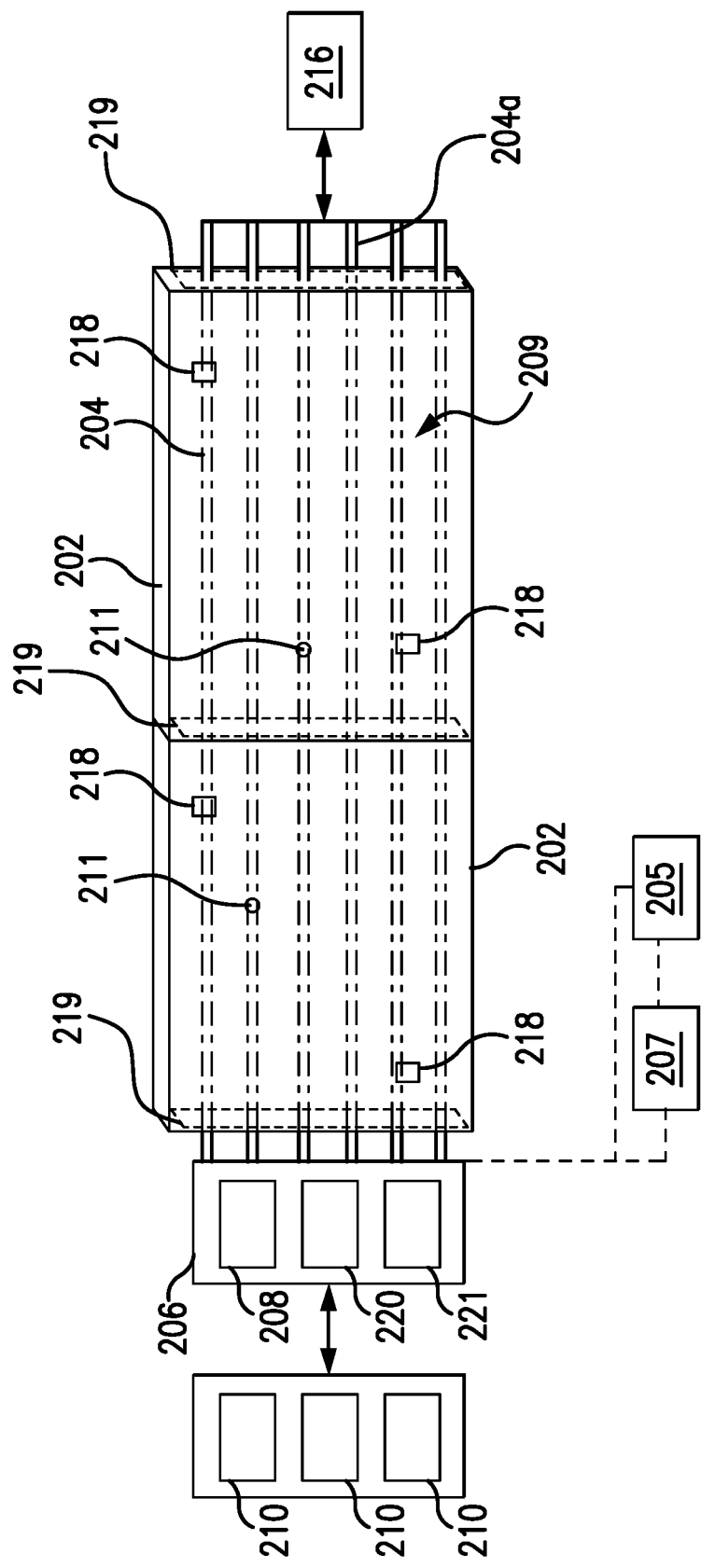
FIG. 2 is a schematic view of another embodiment of a fiber-optic sensing and communication system constructed in accordance with the present disclosure, showing fiber-optic cables operatively connected to the structures.

As shown in FIG. 2, system 200 is shown separate from a VTOL aircraft structure. In this embodiment, system 200 is shown as a generic system that can be applied to a variety of systems or subsystems, whether or not associated with an aircraft. For example, system 200 can be a communication system, an electrical system, a mechanical system, a structural system or any combination thereof. System 200 includes a system hardware element 202, e.g. a structure. System 200 is similar to system 100 in that it too is a system that communicates data within the system and senses physical characteristics associated with the system using a multi-functional fiber-optic sensing and communication network. Each system hardware element 202 has a plurality of fiber-optic cables 204 embedded therein. Hardware element 202 also includes a fiber-optic cable 204a that is operatively connected to hardware element 202, but not embedded within hardware element 202. In other words, hardware element 202 is shown as a hybrid structure with some cables 204 embedded and others not embedded. It is contemplated that fiber-optic cables 204 can be exclusively embedded within hardware elements 202, exclusively outside of hardware elements 202, but operatively connected thereto, or a combination of both.

With continued reference to FIG. 2, fiber-optic cables 204 use sensing elements 211 to modify the existing optical signal in a manner indicative of characteristics of system hardware element 202, e.g. they can act as strain, temperature, or other sensors. Sensing elements 211 inserted into cable 204 can be Fiber Bragg Gratings, or other inherent features that allow physical phenomena such as strain, temperature, pressure, and humidity to be measured using the fiber and appropriate optical components. Multiple fiber-optic cables 204, sensing elements 211, and network controllers 206 allow for reconfiguration without repair in case of damage to one or more of fiber-optic cables 204 or network components, e.g. sensing elements 211, similar to the re-configurability described above. Fiber optical cables 204 extend between one or more adjacent system hardware elements 202, similar to structures 102 and cables 104.

System hardware elements 202 include access points 219 and ports 218, similar to access points 119 and ports 118 described above.

With continued reference to FIG. 2, system 200 includes data sources 216 operatively connected to one or more of cables 204 to communicate data across system 200. Data sources 216 can come from sub-systems, e.g., avionics boxes, health management system, rotor state feedback systems, smart components, digital sensor nodes. System 200 includes a network controller 206 with an interrogator 208 operatively connected to each fiber-optic cable 204 to receive optical energy indicative of structural characteristics of hardware elements 202 therefrom. Interrogator 208 converts the optical energy into electrical signals indicative of the given characteristic of the structure or environment. This allows network controller 206 to monitor characteristics of hardware elements 202 similar to system 100 described above. Network controller 206 includes at least one optical component 220, for example, an amplifier, a connector, a switch, a receiver, a laser diode, a photodiode, and/or a transmitter, optical components 220 are similar to optical components 120 described above.

As shown in FIG. 2, network controller 206 is operatively connected to a processor 207 and/or data storage 205 for storing data therein, receiving data therefrom, or the like. Fiber-optic cables 204 used for structural sensing are also included in a highly redundant, high bandwidth, and reconfigurable communication network, similar to system 100, described above. Network controller 206 includes at least one switch 221 for managing data flow across individual fibers and between multiple fibers to mitigate network failures, similar to system 100, described above.

With continued reference to FIG. 2, a plurality of sensors 210 are operatively connected to fiber-optic cables 204 through network controller 206 to transmit data through the communication network of fiber-optic cables 204. Sensors 210 can also be connected to network controller 206 through a separate fiber-optic cable network or through fiber-optic cables 204. Sensors 210 are similar to sensors 110, described above. Data and/or characteristic data transmitted through fiber-optic cables 204 can be reconfigured by network controller 206, if needed, without physical access, thereby reducing system maintenance and downtime in case of damage to the optical-fiber network.

Figure 3:
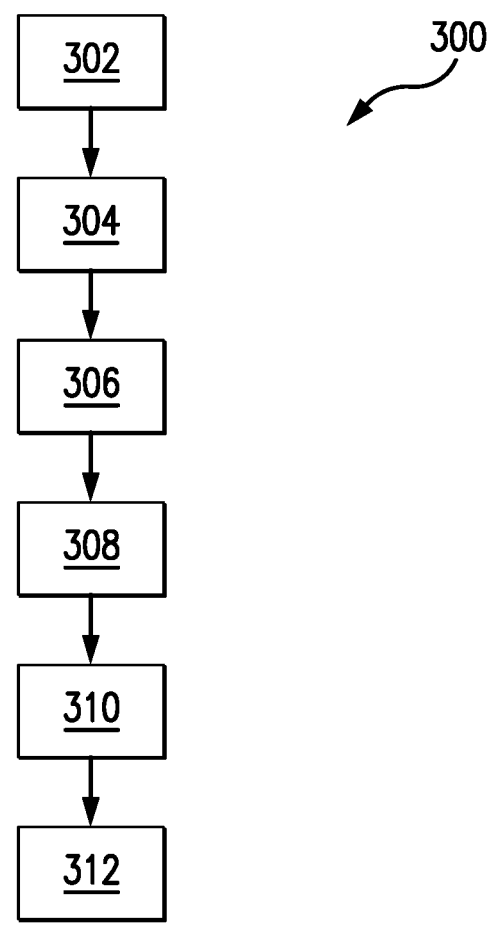
FIG. 3 is a flowchart showing an embodiment of a method for integrally sensing and communicating through a structure.

With reference now to FIG. 3, a method 300 for integrally sensing and communicating through a structure includes transmitting optical energy indicative of a characteristic of a structure, e.g. structure 102 and/or 202, through a fiber-optic cable, e.g. fiber-optic cable 104 and/or 204, to an interrogator, e.g. interrogator 108 and/or 208, in a network controller, e.g. network controller 106 and/or 206, as indicated schematically by box 302.

Method 300 includes transmitting data from a sensor, e.g. sensor 110 and/or 210, and/or a data source, e.g. data source 116 and/or 216, from the network controller through the fiber-optic cable, as indicated schematically by box 304. Transmitting data from the data source can include transmitting avionics data through the fiber-optic cable from the network controller from an avionics system, e.g. avionics system 116, and/or through the fiber-optic cable from the avionics system to the network controller. It is also contemplated that transmitting data from the data source includes transmitting data to the network controller from a health monitoring system, e.g. structural health monitoring system 112, and receiving data therefrom, and can include transmitting rotor data to the network controller from a rotor state feedback system, e.g. rotor state feedback system 114, and receiving data therefrom.

With continued reference to FIG. 3, method 300 includes detecting damage in the fiber-optic cable with the health monitoring system operatively connected to the network controller, as indicated by box 306. The fiber-optic cable can be part of a fiber-optic network, e.g. fiber-optic network 109 and/or 209. Method 300 includes mitigating faults within the fiber-optic network with the network controller by adjusting the configuration of the fiber-optic network to achieve fault tolerance, as indicated by box 308. Adjusting the configuration of the fiber-optic network can include using at least one of an optical switch, e.g. optical switch 221, and/or the network controller to reconfigure the transmitting of optical and/or electrical energy from the fiber-optic cable to a second fiber-optic cable within the fiber-optic cable network, as indicated by box 310. Method 300 includes converting electrical energy to optical energy and optical energy to electrical energy using an interrogator, as indicated by box 312. Those skilled in the art will also readily appreciate that the steps described above can be performed in a variety of different orders, and/or one or more steps can be repeated or excluded as needed.

The methods and systems of the present disclosure, as described above and shown in the drawings, provide for systems and methods for integrally monitoring and communicating across a system, such as an aircraft, with superior properties including reduced maintenance due to system fault tolerance and automatic reconfiguration, and reduction in weight and costs. While the apparatus and methods of the subject disclosure have been shown and described with reference to preferred embodiments, those skilled in the art will readily appreciate that changes and/or modifications may be made thereto without departing from the spirit and scope of the subject disclosure.

What is claimed is:

1. A fiber-optic sensor system comprising: a structure having a fiber-optic cable operatively connected thereto; a network controller having an interrogator operatively connected to the fiber-optic cable to receive optical energy indicative of a characteristic of the structure therefrom and convert optical energy to electrical energy and electrical energy to optical energy for data communication; and at least one of a data source or a sensor operatively connected to the fiber-optic cable through the network controller to transmit data through the fiber-optic cable and receive data therefrom; wherein the data source is at least one of an avionics system or a flight control system to provide data through the fiber optic cable to the network controller and to receive data through the fiber optic cable from the network controller; and, wherein the avionics system includes a health monitoring system and a rotor state feedback system operatively connected to the fiber-optic cable through the network controller to transmit data to the network controller and through the fiber-optic cable and to receive data therefrom.

2. The system as recited in claim 1, wherein the fiber-optic cable is embedded within the structure.

3. The system as recited in claim 1, wherein the structure is one of a plurality of structures wherein the fiber-optic cable extends between adjacent structures.

4. The system as recited in claim 1, wherein the structure includes at least one of an access point to provide physical access to the fiber-optic cable within the structure, or a port to provide connection access to the fiber-optic cable and the network controller.

5. The system as recited in claim 1, further comprising a sensing element inserted within the fiber-optic cable to modify optical energy in a way that is indicative of a characteristic of the structure and transmit the modified optical energy to the network controller.

6. The system as recited in claim 1, wherein the network controller includes at least one optical component selected from a group consisting of an amplifier, a connector, a switch, a receiver, a laser diode, a photodiode and a transmitter.

7. A method for integrally sensing and communicating through a structure, comprising: transmitting optical energy indicative of a characteristic of a structure through a fiber-optic cable to an interrogator in a network controller; and transmitting data from at least one of a sensor or a data source from the network controller through the fiber-optic cable; wherein the data source is at least one of an avionics system or a flight control system to provide data through the fiber optic cable to the network controller and to receive data through the fiber optic cable from the network controller; and, wherein the avionics system includes a health monitoring system and a rotor state feedback system operatively connected to the fiber-optic cable through the network controller to transmit data to the network controller and through the fiber-optic cable and to receive data therefrom.

8. The method as recited in claim 7, further comprising detecting damage in the fiber-optic cable with a health monitoring system operatively connected to the network controller.

9. The method as recited in claim 8, wherein the fiber-optic cable is part of a fiber-optic network, the method further comprising mitigating faults within the fiber-optic network with the network controller by adjusting the configuration of the fiber-optic network to achieve fault tolerance.

10. The method as recited in claim 9, wherein adjusting the configuration of the fiber-optic network includes using at least one of an optical switch or the network controller to reconfigure the transmitting of optical energy from the fiber-optic cable to a second fiber-optic cable within the fiber-optic cable network.

11. The method as recited in claim 7, further comprising converting electrical energy to optical energy and vice versa.

12. The method as recited in claim 7, wherein transmitting data from the data source includes transmitting avionics data through the fiber-optic cable to the network controller from an avionics system.

13. The method as recited in claim 12, wherein transmitting data from the data source includes transmitting data through the fiber-optic cable from the network controller to the avionics system.

14. An aircraft comprising: a structure; a fiber-optic cable operatively connected to the structure; a network controller having an interrogator operatively connected to the fiber-optic cable to receive optical energy indicative of a characteristic of the structure therefrom; and at least one of a data source or a sensor operatively connected to the fiber-optic cable through the network controller to transmit data through the fiber-optic cable and receive data therefrom; wherein the data source is an avionics system to provide avionics data through the fiber-optic cable to the network controller and to receive data through the fiber-optic cable from the network controller; and, wherein the avionics system includes a structural health monitoring system and a rotor state feedback system operatively connected to the fiber-optic cable through the network controller to transmit data to the network controller and through the fiber-optic cable and to receive data therefrom.

15. The aircraft as recited in claim 14, wherein the fiber-optic cable is embedded within the structure.

* * * * *